United States Patent [19]
Hunt

[11] Patent Number: 5,234,569
[45] Date of Patent: Aug. 10, 1993

[54] AIR/FUEL RATIO SENSOR FOR AN INTERNAL COMBUSTION ENGINE

[75] Inventor: Frank W. Hunt, Walled Lake, Mich.

[73] Assignee: Hitachi America, Ltd., Research and Development Division, Tarrytown, N.Y.

[21] Appl. No.: 867,380

[22] Filed: Apr. 13, 1992

[51] Int. Cl.$^5$ ............................................. G01N 27/26
[52] U.S. Cl. ................................... 204/427; 204/424; 204/425; 204/426; 204/428
[58] Field of Search ............... 204/424, 425, 426, 427, 204/428

[56] References Cited

U.S. PATENT DOCUMENTS

| | | |
|---|---|---|
| 4,578,172 | 3/1986 | Yamada et al. ............ 204/426 |
| 4,950,380 | 8/1990 | Kurosawa et al. .......... 204/425 |

Primary Examiner—John Niebling
Assistant Examiner—Bruce F. Bell
Attorney, Agent, or Firm—Gifford, Groh, Sprinkle, Patmore and Anderson

[57] ABSTRACT

A sensor is disclosed for detecting the relative air/fuel ratio of the exhaust gas from an internal combustion engine. The sensor includes a housing which defines a closed interior chamber. An oxygen diffusion cell constructed of a solid electrolytic material has one side exposed to the exhaust gas and a second side exposed to the housing chamber so that oxygen ions flow through the diffusion cell in dependence upon the relative oxygen concentration in both the exhaust gas and the internal air chamber. A sense cell constructed of a solid electrolytic material also has one side exposed to the air chamber and a second side exposed to a substantially constant source of oxygen, such as the atmosphere. Thus, oxygen ion flow through the sense cell varies as a function of the oxygen concentration in the air chamber and thus of the oxygen concentration in the engine exhaust gas. An electronic circuit is electrically connected to the sense cell and generates an output signal representative of both the magnitude and direction of the oxygen ion flow through the sense cell. This electrical output signal is then utilized as an input signal for the fuel system of the engine.

12 Claims, 3 Drawing Sheets

AIR/FUEL RATIO SENSOR FOR AN INTERNAL COMBUSTION ENGINE

BACKGROUND OF THE INVENTION

I. Field of the Invention

The present invention relates generally to electronic sensor and, more particularly, to a sensor for detecting the air/fuel ratio in the exhaust gas of an internal combustion engine.

II. Description of the Prior Art

The operational characteristics of an internal combustion engine, such as those used in automotive engines, are strongly dependent upon the air/fuel (A/F) ratio of the A/F mixture. These operation characteristics are illustrated in FIG. 1 where the air excess ration $\lambda$ is defined by the following equation:

$$\lambda = \frac{(A/F)}{(A/F)_{st}}$$

Where $(AF)_{st}$ is the stoichiometric A/F ratio.

Thus, as shown in FIG. 1, a lean A/F mixture ($\lambda \cdot 1.0$) results in lower fuel consumption rates, lower engine power Band higher $NO_K$ engine emissions than either a rich or stoichiometric A/F mixture. Conversely, a rich A/F mixture ($\lambda < 1.0$) results in greater engine power and higher engine fuel consumption. Simultaneously, a rich A/F mixture results in higher exhaust emissions of carbon monoxide (CO) and lower emissions of $NO_K$.

During the normal operation of an automotive engine, the A/F ratio will vary between rich and lean depending upon the demanded load conditions which would include, for example, acceleration, deceleration, cruise and idle engine conditions. Ideally, the fuel management system for the engine adjusts the A/F ratio of the fuel mixture for optimal engine performance.

With reference now to FIG. 2, the relationship between the air excess ration ($\lambda$) and the exhaust emissions from the internal combustion engine are illustrated. As is evident from FIG. 2, for rich fuel mixtures ($\lambda < 1.10$) the exhaust emissions contain very little oxygen ($O_2$) since the available oxygen has combusted with the fuel. Conversely, the oxygen content for the exhaust emissions increases for a lean A/F mixture ($\lambda > 1.0$) since there is insufficient fuel to combust with the oxygen.

There have been previously known A/F ratio sensors which detect the oxygen content in the exhaust from the engine and, from the oxygen content in the exhaust emissions, determine the A/F ratio for the engine. These previously known sensors typically comprise a solid electrolyte having one side open to a diffusion layer and a second side open to atmospheric air which has a constant oxygen content. The diffusion layer itself contains porous apertures that are exposed to the exhaust gases from the engine. An electronic circuit is then employed to detect both the magnitude and direction of the oxygen ion flow through the solid electrolyte and to provide an electrical output signal representative of this ionic transfer. This output signal is then utilized as an input signal to the fuel management system for the engine.

A primary disadvantage of this previously known type of A/F ratio sensor is that, after extended use, the aperture between the solid electrolyte of the sensor and the exhaust gas emissions becomes contaminated and clogged by particles in the exhaust gas flow. Once the aperture to the solid electrolytic cell is clogged, the sensor may eventually fail and must be replaced.

SUMMARY OF THE PRESENT INVENTION

The present invention provides an A/F ratio sensor which overcomes all of the above-mentioned disadvantages of the previously known devices.

In brief, the sensor of the present invention comprises a housing which defines a closed interior chamber. An oxygen diffusion cell constructed of a solid electrolytic material, such as a zirconia ($ZrO_2$) has one side exposed to the exhaust gas from the engine and its other side exposed to the air chamber. A porous platinum coating is provided on both sides of the diffusion cell while a resistor connected between the platinum coatings allows for the electron exchange necessary for the oxygen ion diffusion through the diffusion cell.

The sensor of the present invention further comprises a sense cell having one side exposed to the air chamber and its other sides exposed to a constant concentration of oxygen, such as the atmosphere. Like the diffusion cell, platinum electrodes are provided on both sides of the sense cell while an electronic circuit is electrically connected to the electrodes on the sense cell which detects both the magnitude and direction of oxygen ion flow through the sense cell. This electrical circuit provides an output signal representative of the direction and magnitude of the ion flow through the sense cell to the fuel management system for the engine.

A heater may also be provided in the housing which maintains a constant temperature for the sense cell, the diffusion cell and well as the air chamber. This heater, by maintaining the temperature of the sense and diffusion cells at or near 700° C., maintains accuracy for the sensor element. Furthermore, since the zirconia must attain a temperature of about 400° C. before ionic exchange can occur, the heater enables operation of the sensor during engine startup.

Also, a porous diffusion layer (such as $MgAl_2O_4 + SiO_2$) may be formed on the sense electrode and/or diffusion cell for controlling the gas diffusion rate. This layer(s) may be used so that the gas flow is properly diffusion limited. This layer will be on the inside of the air chamber as to avoid contamination from exhaust emissions.

In practice, under lean A/F exhaust gas conditions ($\lambda > 1.0$), excess oxygen ions diffuse from the exhaust gas, through the diffusion cell and to the air chamber thereby increasing the oxygen concentration within the air chamber. This increased oxygen concentration within the air chamber causes oxygen ions to diffuse through the sense cell to the atmosphere. This diffusion of oxygen ions through the sense cell causes an electron current flow through the sense cell which is detected by the electronic circuit which provides an output signal to the fuel management system for the internal combustion engine.

Conversely, during a rich A/F ratio ($\lambda < 1.10$) oxygen ions diffuse from the air chamber through the diffusion cell and react with the exhaust combustible, hydrogen, carbon monoxide and hydrocarbons by a catalytic reaction at the platinum electrode. This depletion of oxygen from the air chamber in turn causes oxygen ions to diffuse from atmosphere, through the sense cell and to the air chamber. In doing so, the direction of current flow between the sense cell electrodes is reversed and this reversal, together with the magnitude of the current flow through the sense cell, is detected by the electronic circuit and provided as an input signal to the fuel management system.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 3:
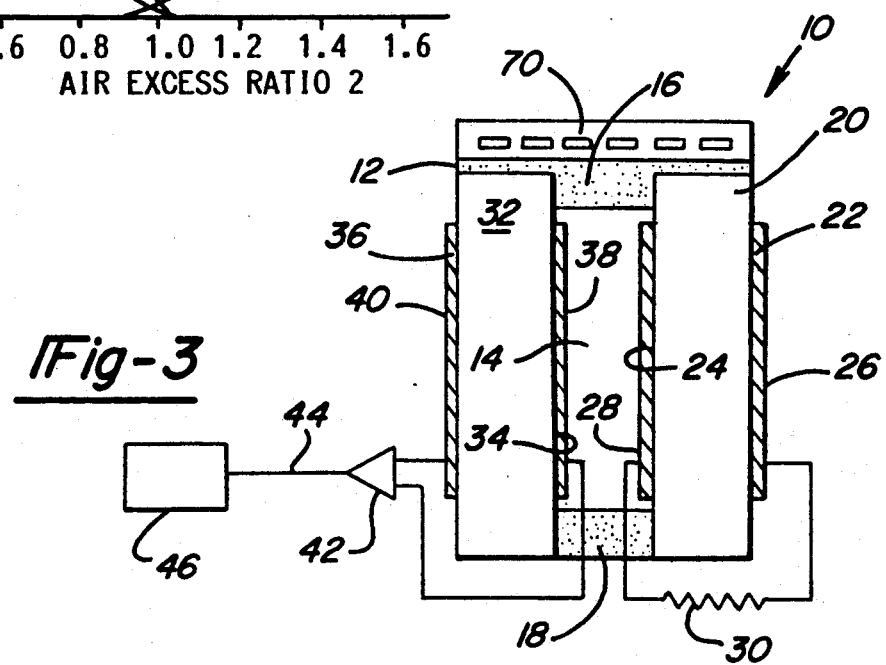
FIG. 3 is a cross-sectional view illustrating a preferred embodiment of the sensor of the present invention.

With reference now to FIG. 3, the preferred embodiment of the A/F ratio sensor 10 of the present invention is thereshown and comprises a housing 12 defining a closed air chamber 14. The housing 12 also includes a pair of spacers 16 and 18 which are constructed of an electrical insulating material. The actual shape of the housing, i.e. round, flat, rectangular, conical, etc., is not critical.

A diffusion cell 20 has one side 22 which is exposed to the exhaust gases from the internal combustion engine (not shown). The opposite side 24 of the diffusion cell 20 is exposed to the air chamber 14.

The diffusion cell 20 is constructed of a solid electrolytic material capable of diffusing oxygen ions. Preferably, the diffusion cell is constructed from zirconium oxide (ZrO$_2$) although other materials can alternatively be used. In addition, an electrode 26 is provided on the side 22 of the diffusion cell 20 while a second electrode 28 is provided on the side 24 of the diffusion cell 20. Preferably, the electrodes 26 and 28 are constructed of porous material, such as platinum.

Still referring to FIG. 3, a resistor 30 is electrically connected between the electrodes 26 and 28. This resistor 30 allows for the electron exchange to occur between the electrodes 26 and 28 which occurs during oxygen ion diffusion through the diffusion cell 20.

The sensor 10 further comprises a sense cell 32 constructed of a solid electrolytic material capable of diffusing oxygen ions. The sense cell 32, like the diffusion cell 20, is preferably constructed of ziconium oxide.

One side 34 of the sense cell 32 is exposed to the air chamber 14 while the opposite side 36 of the sense cell 32 is exposed to a reference concentration of oxygen, such as the atmosphere.

An electrode 38, preferably constructed of porous material, such as platinum, is provided on the side 34 of the sense cell 32. Similarly, a second electrode 40, preferably constructed of porous material, such as platinum, is provided on the opposite side 36 of the sense cell 32.

An electronic circuit 42, illustrated as a differential amplifier for simplicity, is connected to the sense cell electrodes 38 and 40. Thus, an output 44 from the circuit 42 provides an electronic signal representative of both the magnitude and direction of current flow between the sense cell electrodes 38 and 40. This output 44 is connected as an electrical input signal to a fuel management system 46 for the engine (not shown).

A heater 70 may be provided in the housing 12 which maintains the temperature of the diffusion cell 20, sense cell 32 and housing chamber 14 at about 700° C. in order to maintain sensor accuracy. Any conventional electrical heater can be used. Furthermore, the heater 70 rapidly heats the diffusion cell 20 and sense cell 32 to over 300° C., necessary for ionic transfer, to sooner enable sensor operation during engine startup.

Figure 1:
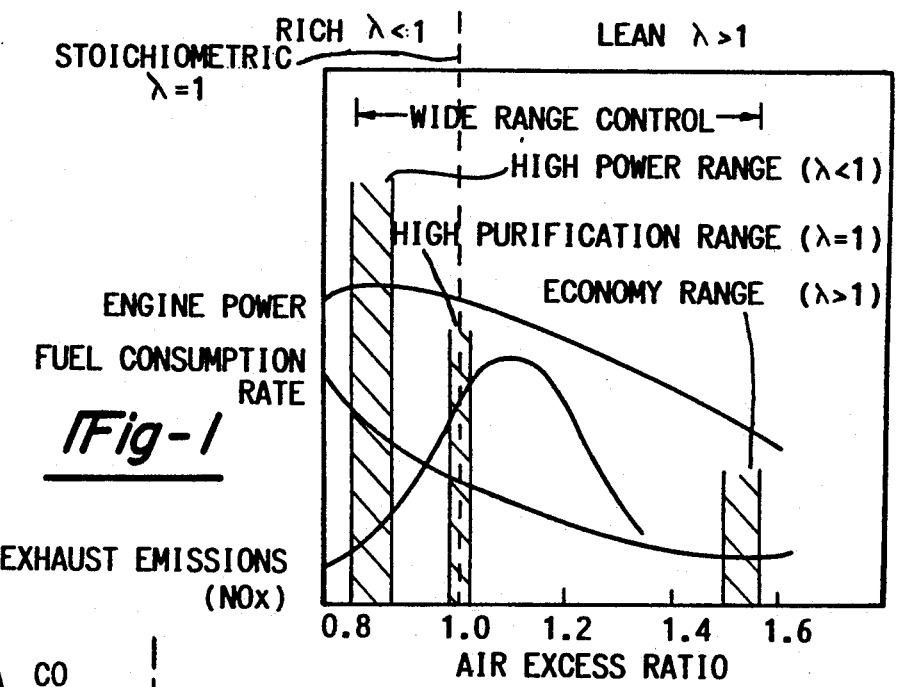
FIG. 1 is a chart illustrating the air excess ratio and its relation to engine performance parameters.
Figure 2:
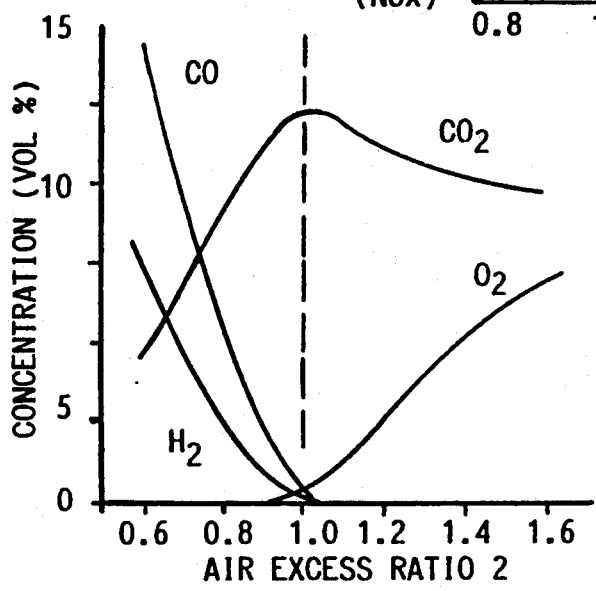
FIG. 2 is a graph illustrating the relationship between the engine exhaust emissions and the air excess ratio $\lambda$.
Figure 4:
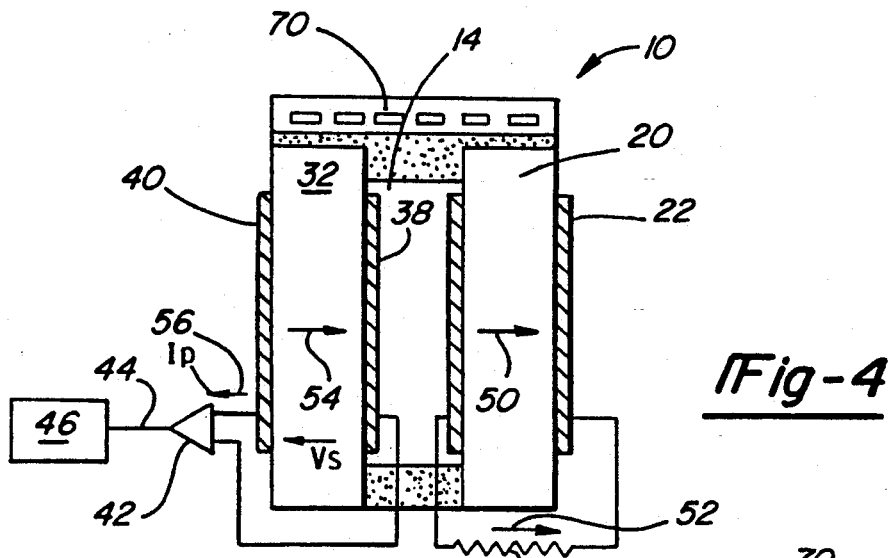
FIG. 4 is a diagrammatic view similar to FIG. 3, but illustrating the operation of the sensor element during a rich A/F mixture engine condition.

With reference now to FIG. 4, the operation of the sensor of the present invention will now be described during a rich A/F engine mixture. During such an engine operating condition, as shown in FIG. 2, the exhaust gas emissions are depleted of oxygen. Consequently, oxygen ions flow from the air chamber 14 in the direction of arrow 50 to the side 22 of the diffusion cell 20 whereupon the oxygen reacts with the combustible products in the exhaust gas. Simultaneously, the oxygen ion flow through the diffusion cell 20 causes a current flow through the resistor in the direction indicated by arrow 52.

Simultaneously, due to the depletion of oxygen ions in the air chamber 14, oxygen ions diffuse through the sense cell 32 from the atmosphere and towards the air chamber 14 and thus in the direction of arrow 54. This in turn causes a current flow ($I_P$) in the electronic circuit 42 in the direction of arrow 56. The magnitude of the current flow 56 will vary in proportion to the rate of ion flow through the sense cell 32 and thus as a fraction of the air excess ratio $\lambda$.

Figure 5:
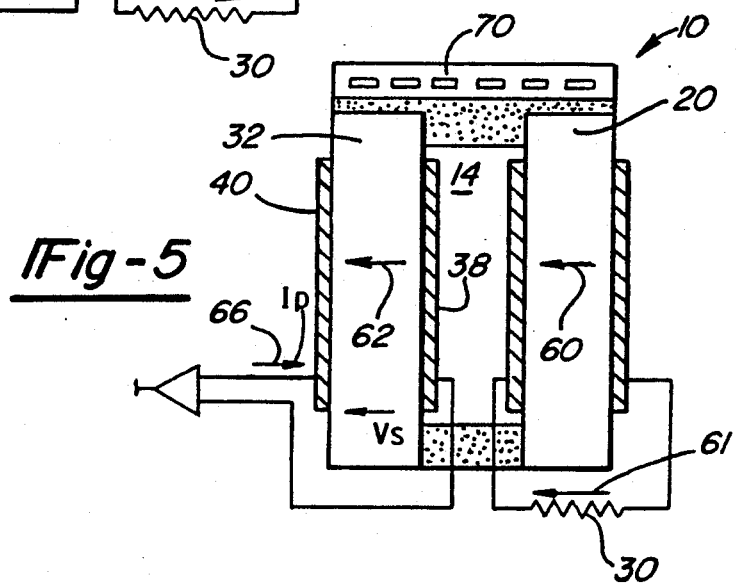
FIG. 5 is a view similar to FIG. 4 but illustrating the operation of the sensor of the present invention during a lean A/F engine condition.

With reference now to FIG. 5, the operation of the sensor 10 of the present invention is thereshown during a lean A/F engine condition. During such a condition, the exhaust gases contain excess oxygen which diffuses through the diffusion cell 20 in the direction of arrow 60 and thus toward the air chamber 14. Current flow in the direction of arrow 61 through the resistor 30 completes the ion exchange necessary for the oxygen ion diffusion so that the oxygen concentration in the air chamber 14 increases.

The increased concentration of oxygen within the air chamber 14 causes oxygen ions to diffuse through the sense cell 32 in the direction of arrow 62 which, in turn, causes a current flow ($I_P$) through the electronic circuit 42 as depicted by arrow 66. The magnitude of this current flow 66 is directly proportional to the rate of ion exchange through both the diffusion cell 20 and the sense cell 32 which is proportional to the oxygen concentration in the exhaust gases and thus proportional to the air excess ratio $\lambda$. Furthermore, as can be seen by a comparison of FIGS. 4 and 5, the direction of the current flow 66 during a lean A/F mixture is opposite from the direction of current flow during a rich A/F mixture.

Figure 6:
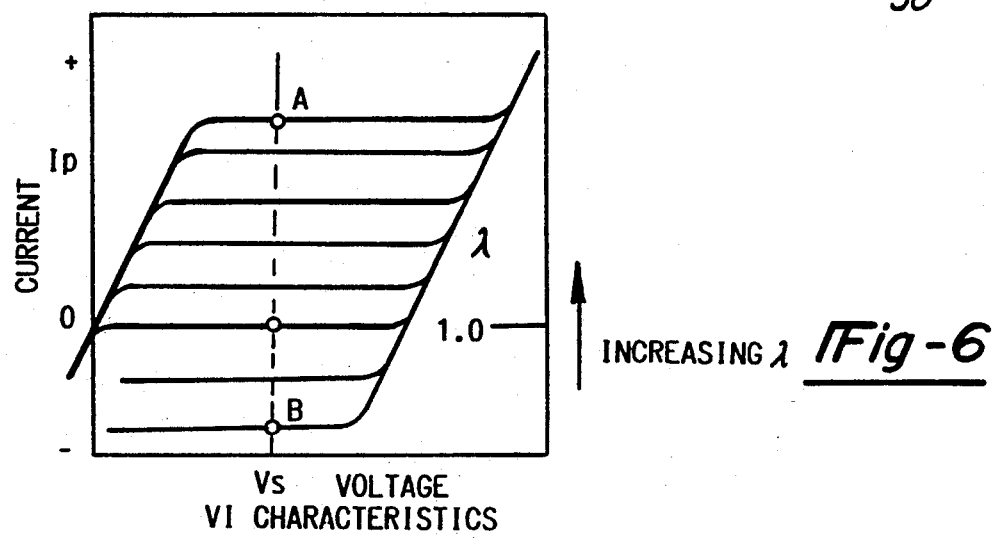
FIG. 6 is a graph illustrating the current flow through the sense cell for different air excess ratios ($\lambda$)

With reference now to FIGS. 5 and 6, when the DC voltage is supplied between the opposing electrodes 38 and 40 in the direction of arrow $V_S$, the current $I_P$ appears in the sense cell 32 which was pre-heated to the working temperature. In the zirconia solid electrolyte, the $I_P$ is pumped out of the detecting electrode 38 to the reference electrode 40 (FIG. 5) as oxygen ions.

However, the oxygen ion attracts electrons near the detecting electrode 38 and are pumped out to the electrolyte, thereby causing the shortage of oxygen ions. Accordingly, oxygen gas comes into the air chamber 14 through the diffusion cell 20 with a limited speed of diffusion. At the equilibrium state, the pumping current amount of the oxygen ions is equal to the flow amount of the oxygen gas at the limited diffusion speed.

With reference particularly to FIG. 6, the sense cell current $I_P$ is thereshown as a function of the air excess ratio $\lambda$. Thus, for rich air/fuel mixtures ($\lambda < 1$) current flow $I_P$ is negative. Conversely, a positive current flow $I_P$ occurs for lean air/fuel mixtures ($\lambda > 1$). In both cases, the sense cell operates in a limited current mode.

At a stoichiometric point, oxygen, as well as $H_2$, CO and HC preferably becomes very thin so that the $I_P$ does not flow and the voltage between the electrodes is the electromotive force of the cell.

Figure 7:
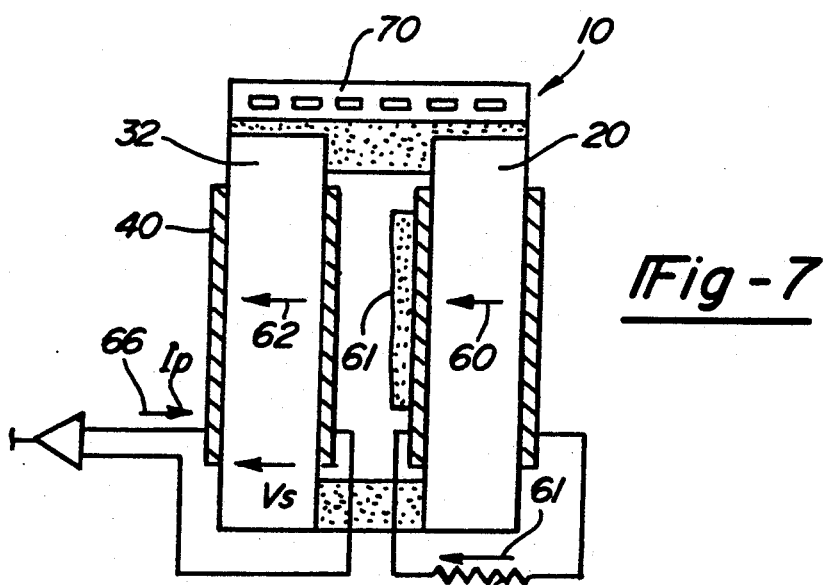
FIGS. 7-9 are all cross sectional views similar to FIG. 3, but each illustrating a different modification thereof.
Figure 8:
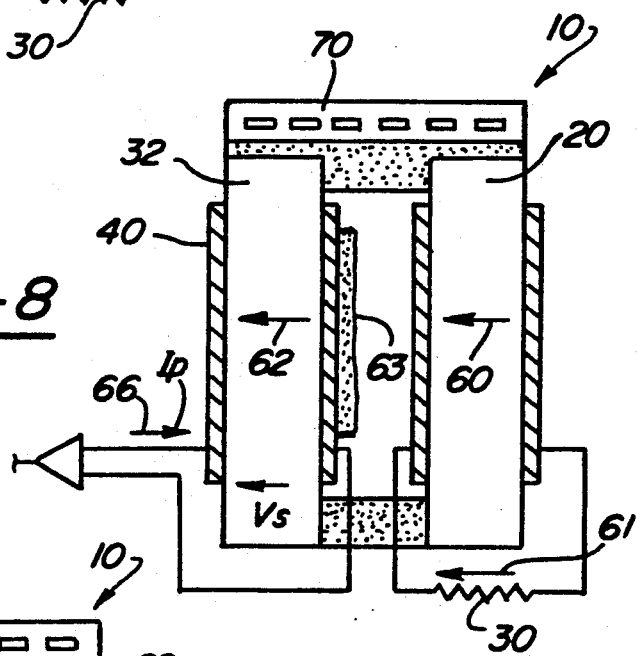
Figure 9:
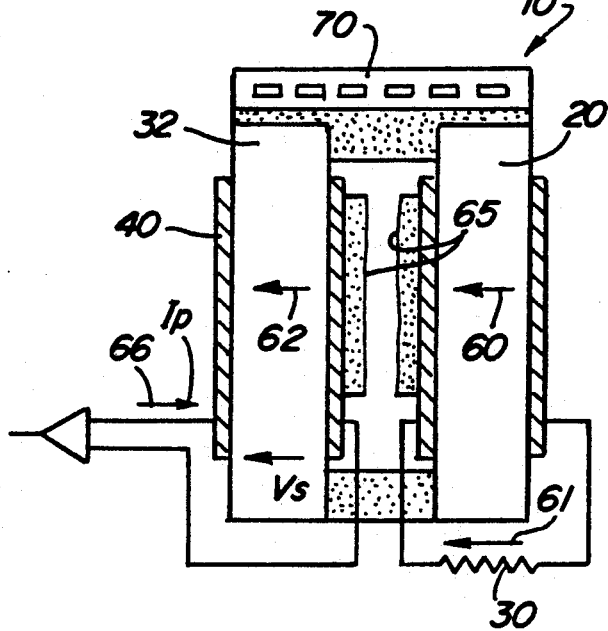

FIGS. 7, 8 and 9 show modifications that may be added to the sensor design. FIG. 7 shows a porous diffusion layer 61 (such as $MgAl_2O_4 + SiO_2$) on the sense cell for controlling the gas diffusion rate. Furthermore, FIG. 9 shows a porous diffusion layer 65 (such as $MgAl_2O_4$) on both the diffusion cell and the sense cell for controlling the gas diffusion rate.

This layer(s) may be used so that the gas flow is properly diffusion limited. The diffusion layer will be on the inside of the air chamber so to avoid contamination from exhaust emissions which is a problem with previously known devices.

From the foregoing, it can be seen that the present invention provides a simple and yet highly effective A/F sensor for use with the exhaust gases of an internal combustion engine. Furthermore, unlike the previously known A/F sensors, clogging of any diffusion aperture is completely eliminated.

Having described our invention, many modifications thereto will become apparent to those skilled in the art to which it pertains without deviation from the spirit of the invention as defined by the scope of the appended claims.

I claim:

1. A sensor for detecting the air/fuel ratio of the exhaust gas from an internal combustion engine comprising:

a housing, said housing defining a closed air chamber, said air chamber being fluidly sealed from the exhaust gas, an oxygen diffusion cell constructed of an electrolytic material, said diffusion cell having one side exposed to the exhaust gas and a second side open to said air chamber, a sense cell constructed of an electrolytic material, said sense cell having one side open to said chamber and a second side open to a constant reference source of oxygen so that oxygen ion flow through said sense cell varies as a function of the oxygen concentration in said housing chamber, means for detecting the direction and magnitude of oxygen ion flow through said sense cell and for generating an electrical output signal representative thereof.

2. The invention as defined in claim 1 wherein said detecting means comprises a pair of electrodes attached to said sides of said sense cell so that said sense cell and said electrodes form an electrochemical cell, and electronic circuit means connected to said electrodes which generates said electronic signal.

3. The invention as defined in claim 2 wherein said electrodes are comprised of a porous material.

4. The invention as defined in claim 3 wherein said porous material comprises platinum.

5. The invention as defined in claim 1 and comprising a pair of electrodes attached to said sides of said diffusion cell, and an electronical resistor connected between said electrodes to conduct electrons resulting from ion diffusion through said diffusion cell between said electrodes.

6. The invention as defined in claim 1 and comprising means for heating said diffusion cell.

7. The invention as defined in claim 1 and comprising means for heating said sense cell, said diffusion cell and said interior chamber.

8. The invention as defined in claim 1 wherein said diffusion cell comprises zirconium oxide.

9. The invention as defined in claim 1 wherein said sense cell comprises zirconium oxide.

10. The invention as defined in claim 1 wherein said reference source of oxygen comprises atmospheric air.

11. The invention as defined in claim 1 and comprising a diffusion layer on said sense cell.

12. The invention as defined in claim 1 and comprising a diffusion layer on said diffusion cell.

* * * * *

UNITED STATES PATENT AND TRADEMARK OFFICE
CERTIFICATE OF CORRECTION

PATENT NO. : 5,234,569
DATED : August 10, 1993
INVENTOR(S) : Frank W. Hunt

It is certified that error appears in the above-indentified patent and that said Letters Patent is hereby corrected as shown below:

Column 1, line 24, ($\lambda$ 1.0) should be --($\lambda$>1.0)--.

Column 1, line 26, "Band" should be --and--.

Column 1, line 49, after "exhaust" insert --emissions--.

Column 2, line 58, "<1.10)" should be --<1.0)--.

Column 4, line 39, "fraction" should be --function--.

Column 5, line 25, "sense" should be --diffusion--.

Column 5, line 25, after "rate." add --FIG. 8 shows a porous diffusion layer 63 (such as $MgAl_2O_4$ + $SiO_2$) on the sense cell for controlling the gas diffusion rate.--

Column 5, line 27, "$MgAl_2O_4$" should be --$MgAl_2O_4$ + $SiO_2$--.

Column 6, line 30, "electronical" should be --electrical--.

Signed and Sealed this

Twenty-fourth Day of January, 1995

Attest:

BRUCE LEHMAN

Attesting Officer

Commissioner of Patents and Trademarks